Nov. 23, 1943. E. N. FRAZEE Plant Pat. 609
FREESIA VARIETY
Filed July 28, 1943
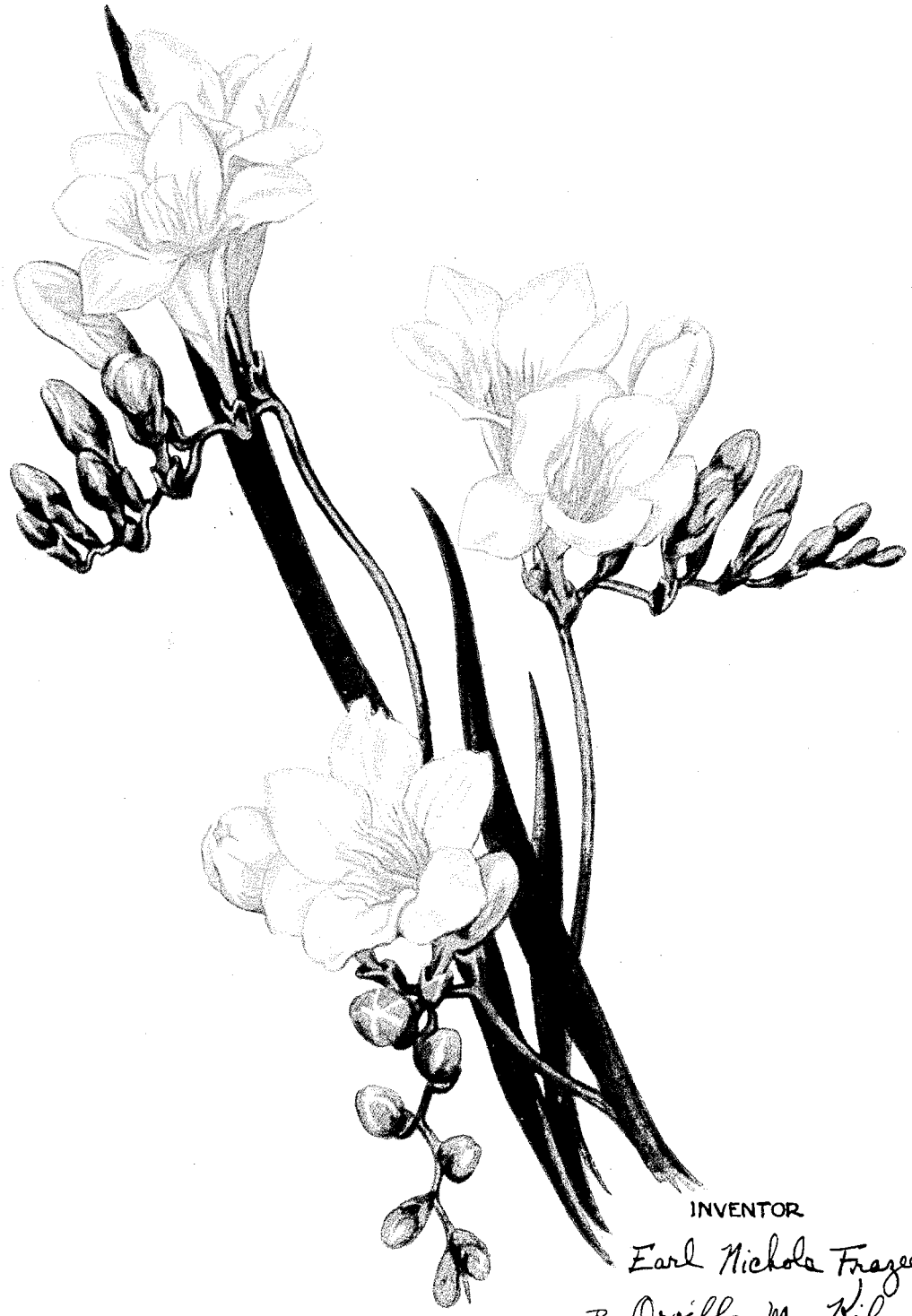
INVENTOR
Earl Nichols Frazee
By Orville M. Kile
PLANT PATENT AGENT Patented Nov. 23, 1943

Plant Pat. 609

UNITED STATES PATENT OFFICE

609

FREESIA VARIETY

Earl Nichols Frazee, Oceanside, Calif.

Application July 28, 1943, Serial No. 496,497

1 Claim. (Cl. 47—60)

My present invention pertains to improvements in freesia plants, particularly of white varieties. The object of my invention is the production of an early-blooming white freesia variety, vigorous and tall of growth, and producing large fragrant flowers.

This variety resulted from hybridizing experiments regularly conducted by me. I do not keep a definite lineage record of my crosses, therefore cannot tell the parentage of this new variety. But I plant seeds from desirable varieties which have been cross-fertilized, then when the resulting plants have bloomed, select desirable seedlings. The present variety is one of these seedlings which I have selected.

My new variety grows to the proportions of a "giant freesia" when forced in a greenhouse, although it is scarcely more than half as tall when grown outdoors. It is substantially pure white and very fragrant. One of its most outstanding qualities is its excellent keeping ability. Its foliage is 4 to 6 inches shorter than the flower stems, thus does not interfere with the display of the blossoms or with cutting them. Its blooming season is very early in comparison with similar varieties. When grown in the field in Southern California, its blooming dates are approximately from February 15 to March 1.

The original illustration which is a part of this specification shows sprays of my new variety of freesia in natural colors but considerably reduced in size.

Following is a detailed description of the flower and plant of this new freesia variety:

*The plant*

Growth: Healthy and vigorous. Grown outdoors, the average height is 10 to 12 inches. Forced in a greenhouse, it attains a height of as much as 24 inches.

Blooming habits: Blooming season is earlier than for similar white varieties. Usual season is from February 15 to March 1 when grown outdoors in this climate. Produces many large flowers.

Stems: Heavy; rigid; tall; dark green; average length about 18 inches, bearing flowers well above the foliage.

Foliage: Plentiful; dark rich green; gradually tapering to a point; ⅝ inch wide at broadest point; four to six inches shorter than flower spike.

Bracts: Clinging; substantial; dark green.

*The flower*

Size: Very large. Average width of open flower is 2 inches for greenhouse-grown specimens. Average length of flower tube is 1½ inches.

Form: Funnel-shaped, with considerable constriction of lower portion of tube. Petals spread wide at top.

Color: Pure white, with soft touch of yellow and tracings of green in the throat. Outer surface of tube is tinged with yellow and slight tracings of green.

Fragrance: Delightful and distinct.

Arrangement: Flowers are borne on sturdy, upright stems along a jointed rachis which extends almost at right angles to the stem. Spikes have an exceptionally large number of blooms, six to nine closely placed buds and blossoms making up each spike. As many as four blossoms to a spike are open and fresh at one time.

Petals or lobes: Six; rounded; slightly overlapping; very substantial in texture.

Stamens: Three; greenish-white, with light yellow anthers.

Pistils: Inconspicuous; divided.

Persistence: Exceptionally good lasting qualities. After cutting, the buds will all bloom out and last for considerably more than a week.

*Comparison*

The variety which is most like my new variety is Freesia Tecolote White. But these two varieties differ, principally in the following respects:

1. The flowers of my new variety are larger and more open and widespread.
2. The flowers of my new variety are of much heavier substance.
3. The stems of my new variety are much heavier and stronger.
4. The blossoms of my new variety have much better lasting quality when cut.
5. The blooming season of my new variety is about ten days earlier when grown under similar conditions.

Having thus disclosed my invention, I claim:

The new and improved variety of freesia plant herein shown and described, characterized particularly by its healthy, vigorous, upright growth; its very early blooming season; its strong, heavy and rigid stems; its many large, fragrant blossoms of heavy substance, excellent keeping qualities, and predominantly white color.

EARL NICHOLS FRAZEE.